(12) United States Patent
Fan et al.

(10) Patent No.: US 9,125,707 B2
(45) Date of Patent: Sep. 8, 2015

(54) CANNULATED GUIDE TOOLS

(75) Inventors: Wei Li Fan, Malden, MA (US); Michael Charles Ferragamo, Foster, RI (US); James Joseph Sullivan, Shrewsbury, MA (US)

(73) Assignee: Smith & Nephew, Inc., Memphis, TN (US)

( * ) Notice: Subject to any disclaimer, the term of this patent is extended or adjusted under 35 U.S.C. 154(b) by 570 days.

(21) Appl. No.: 12/986,004

(22) Filed: Jan. 6, 2011

(65) Prior Publication Data

US 2012/0179146 A1 Jul. 12, 2012

(51) Int. Cl.
*A61B 17/88* (2006.01)
*A61B 17/04* (2006.01)
*A61B 17/00* (2006.01)
*A61B 17/29* (2006.01)

(52) U.S. Cl.
CPC ......... *A61B 17/8861* (2013.01); *A61B 17/0469* (2013.01); *A61B 17/0482* (2013.01); *A61B 2017/00469* (2013.01); *A61B 2017/2927* (2013.01)

(58) Field of Classification Search
CPC ........... A61B 17/0469; A61B 17/8869; A61B 17/8861
USPC ............................ 606/103, 139, 144, 145, 83
See application file for complete search history.

(56) References Cited

U.S. PATENT DOCUMENTS

| | | |
|---|---|---|
| 4,917,699 A | 4/1990 | Chervitz |
| 4,960,134 A | 10/1990 | Webster, Jr. |
| 5,231,989 A | 8/1993 | Middleman et al. |
| RE34,502 E | 1/1994 | Webster, Jr. |
| 5,289,963 A | 3/1994 | McGarry et al. |
| 5,345,937 A | 9/1994 | Middleman et al. |
| 5,356,064 A | 10/1994 | Green et al. |
| 5,364,002 A | 11/1994 | Green et al. |
| 5,366,479 A | 11/1994 | McGarry et al. |

(Continued)

FOREIGN PATENT DOCUMENTS

| | | |
|---|---|---|
| EP | 0 643 945 A2 | 3/1995 |
| EP | 1 444 959 A | 8/2004 |

(Continued)

OTHER PUBLICATIONS

International Search Report, PCT/US2012/020240, dated, Apr. 27, 2012, pp. 1-3.

(Continued)

*Primary Examiner* — Eduardo C Robert
*Assistant Examiner* — Julianna N Harvey
(74) *Attorney, Agent, or Firm* — Burns & Levinson LLP; Joseph M. Maraia

(57) ABSTRACT

According to a first configuration, a hand tool is configured to include a shaft, a handle disposed at a proximal end of the shaft, and a tubular tip disposed on a hinge at a distal end of the shaft. The tubular tip pivots about the hinge, providing a way to steer a resource to a specific location in a medical site. In accordance with a second configuration, a hand tool includes a flexible section of tube, a flexible sheathing, and a link. The flexible sheathing encases the flexible section of tube. At least a portion of the link resides between an outer surface of the flexible section of tube and an inner surface of the flexible sheathing. One end of the link is affixed to a distal tip of the flexible section of tube. Pulling on the link causes the flexible section of tube to arc.

18 Claims, 19 Drawing Sheets

(56) References Cited

U.S. PATENT DOCUMENTS

| | | | |
|---|---|---|---|
| 5,484,095 | A | 1/1996 | Green et al. |
| 5,497,933 | A | 3/1996 | DeFonzo et al. |
| 5,549,617 | A * | 8/1996 | Green et al. .................. 606/144 |
| 5,562,689 | A * | 10/1996 | Green et al. .................. 606/151 |
| 5,584,839 | A | 12/1996 | Gieringer |
| 5,817,109 | A | 10/1998 | McGarry et al. |
| 5,865,361 | A | 2/1999 | Milliman et al. |
| 6,079,606 | A | 6/2000 | Milliman et al. |
| 6,136,010 | A | 10/2000 | Modesitt et al. |
| 6,241,139 | B1 | 6/2001 | Milliman et al. |
| 6,330,965 | B1 | 12/2001 | Milliman et al. |
| 6,450,948 | B1 | 9/2002 | Matsuura et al. |
| 6,491,645 | B1 | 12/2002 | Gaber |
| 6,669,073 | B2 | 12/2003 | Milliman et al. |
| 6,840,932 | B2 | 1/2005 | Lang |
| 6,953,139 | B2 | 10/2005 | Milliman et al. |
| 6,964,668 | B2 | 11/2005 | Modesitt et al. |
| 7,001,400 | B1 | 2/2006 | Modesitt et al. |
| 7,112,208 | B2 | 9/2006 | Morris et al. |
| 7,235,087 | B2 | 6/2007 | Modesitt et al. |
| 7,303,107 | B2 | 12/2007 | Milliman et al. |
| 7,481,824 | B2 | 1/2009 | Boudreaux et al. |
| 7,565,993 | B2 | 7/2009 | Milliman et al. |
| 7,624,902 | B2 | 12/2009 | Marczyk et al. |
| 7,624,903 | B2 | 12/2009 | Green et al. |
| 7,681,772 | B2 | 3/2010 | Green et al. |
| 7,828,187 | B2 | 11/2010 | Green et al. |
| 2002/0019649 | A1 | 2/2002 | Sikora et al. |
| 2002/0117533 | A1 | 8/2002 | Milliman et al. |
| 2002/0117534 | A1 | 8/2002 | Green et al. |
| 2002/0143354 | A1 * | 10/2002 | Lang .............................. 606/167 |
| 2003/0083695 | A1 | 5/2003 | Morris et al. |
| 2003/0093093 | A1 | 5/2003 | Modesitti et al. |
| 2004/0147932 | A1 | 7/2004 | Burkinshaw et al. |
| 2005/0033365 | A1 | 2/2005 | Courage |
| 2005/0165420 | A1 * | 7/2005 | Cha ................................ 606/150 |
| 2005/0177179 | A1 * | 8/2005 | Baynham et al. ............. 606/151 |
| 2005/0222601 | A1 | 10/2005 | Erhard |
| 2005/0228399 | A1 | 10/2005 | Kubo et al. |
| 2005/0261692 | A1 * | 11/2005 | Carrison et al. ................ 606/79 |
| 2006/0041263 | A1 * | 2/2006 | Chu et al. ....................... 606/144 |
| 2006/0119014 | A1 * | 6/2006 | Towers et al. ................. 264/536 |
| 2007/0152014 | A1 | 7/2007 | Gillum et al. |
| 2007/0179340 | A1 | 8/2007 | Jorgensen |
| 2007/0282358 | A1 | 12/2007 | Remiszewski et al. |
| 2008/0188859 | A1 | 8/2008 | Reitzig et al. |
| 2009/0157081 | A1 | 6/2009 | Homan et al. |
| 2010/0030029 | A1 | 2/2010 | Markham |
| 2010/0042106 | A1 * | 2/2010 | Bryant et al. .................. 606/103 |
| 2010/0057077 | A1 | 3/2010 | Ducharme |

FOREIGN PATENT DOCUMENTS

| | | |
|---|---|---|
| WO | WO99/56628 | 11/1999 |
| WO | WO 02/36020 A1 | 5/2002 |
| WO | WO 2005/037150 A1 | 4/2005 |
| WO | WO 2006/088452 A2 | 8/2006 |

OTHER PUBLICATIONS

International Preliminary Report from corresponding International Application No. PCT/US2012/020240 mailed Jul. 10, 2013, pp. 14.

* cited by examiner

CANNULATED GUIDE TOOLS

BACKGROUND

The prior art appears to include different types of hand tools to carry out surgical procedures. For example, one type of hand tool may be used to make an incision in human tissue, another type of hand tool may be used to drill into a bone, another type of hand tool may be used to cut away cartilage, another type of hand tool may be used suture tissue back together, etc.

Surgical procedures, such as bone repair, may require guiding a wire through a hole drilled in a bone. Subsequent to drilling a hole in a bone, it may be difficult to steer a wire through the hole because an incision made in tissue may naturally close or there may not be easy access to the drilled hole through the incision because the drilled hole is behind an obstruction such as another bone.

BRIEF DESCRIPTION

Embodiments herein include multiple types of novel cannulated guide tools for use in various applications.

For example, in accordance with a first embodiment, a hand tool is configured to include a shaft, a handle disposed at a proximal end of the shaft, and a tubular tip disposed on a hinge at a distal end of the shaft. The tubular tip pivots about the hinge, thus providing a way to steer a resource such as a guide wire to a specific location in a medical site.

The hand tool can include a link extending between the handle and the tubular tip. In accordance with such an embodiment, the link controls an angular orientation of the tubular tip about the hinge at the distal end of the shaft. As an example, during use, a user squeezes the handle disposed at a proximal end of the hand tool to control an angular position of a hinged, tubular tip at a distal end of the hand tool.

In one embodiment, the link is a slidable link. The slidable link extends between the handle and the tubular tip of the hand tool. Squeezing of the handle causes the slidable link to move axially along the rigid tube to control an angular orientation of the tubular tip with respect to a lengthwise axis of the shaft.

The tubular tip can include a lug assembly in a vicinity of the hinge. In such an embodiment, the slidable link at the distal end of the shaft is in contact with the lug to adjust an angular offset of the tubular tip with respect to a rigid tube in the shaft.

In accordance with yet further embodiments, the hinge of the hand tool is formed by and includes protrusions (e.g., projections) on the tubular tip. The protrusions can be mated to dimples disposed on the shaft at the distal end of the hand tool to form a hinge. In one example embodiment, the tubular tip includes a spacing between the protrusions enabling the projections in tubular tip to be compressed. The projections of the tubular tip pressably fit into the dimples to form hinge on which the tip rotates.

In a more specific example embodiment, the handle is a scissors handle. The shaft can include a rigid tube extending from the proximal end of the shaft to the distal end of the shaft. The tubular tip on the hinge extends beyond the distal end of the shaft to form a movable and angularly adjustable extension of the rigid shaft.

The scissors handle can include a first lever and a second lever. The first lever of the scissors handle can be fixedly attached to the shaft. The second lever of the scissors handle pivots about the first lever of the scissors handle and is mechanically coupled to the link. Based on movement of the second lever with respect to the first lever, the link slides axially along a length of the shaft to adjust the angular orientation of the tubular tip. Thus, the angular orientation of the tubular tip can be configured to vary depending on an angular orientation of the first lever with respect to the second lever. In other words, depending on a degree of squeezing the scissors handle, the slidable link controls the tubular portion in the hinged tip to be axially aligned or angularly offset with respect to the rigid tube attached to the scissors handle.

In one configuration, when a straight tubular region of the tubular section in the hinged tip is positioned to axially align with the rigid tube of the hand tool to form a straight tubular guide, there is an open space or notched region between the tubular portion in the hinged tip and the end of the rigid tube. Thus, the hand tool can be configured to include a gap or open space between the tubular portion in the hinged tip and the end of the rigid tube in the shaft. When the hinged tip is positioned off axis or angularly offset with respect to the axis of the rigid tube via squeezing the scissor handle, a size of the gap or open space between the end of the rigid tube and the tubular portion of the hinged tip increases.

In one embodiment, the hand tool as discussed herein is used to steer a guide wire into a hole drilled into a bone. For example, an operator receives the hand tool as discussed above. The operator inserts and slides a guide wire through the rigid tube in the hand tool starting at a handle end (e.g., proximal end) of the hand tool. The operator pushes the wire through the rigid tube and through the hinged tubular tip at the distal end of the hand tool. Based on a degree of squeezing the handle during an operation, the operator can adjust the tip at the distal end of the hand tool to steer the end of the guide wire to a desired location such as a hole drilled in a bone.

Embodiments herein further include manufacture or assembly of the hand tool as discussed herein. This can include receiving a shaft; affixing a handle to a proximal end of the shaft; and disposing a tubular tip on a hinge at a distal end of the shaft.

In accordance with a second embodiment, a hand tool can be configured to include a tubular guide, a flexible sheathing, and a link. The tubular guide can be configured to include a rigid section of tube coupled to a flexible section of tube. The flexible sheathing covers at least a portion of the tubular guide. The link can be a slender, flexible material such as wire, string, cable, thread, etc. and thus slide alongside the rigid section of tube and flexible section of tube. In one embodiment, the slidable link extends along a length of the tubular guide between an outer surface of the tubular guide and an inner surface of the flexible sheathing. One end of the slidable link is affixed to a distal tip of the flexible section of tube. In accordance with such an embodiment, the act of pulling on the slidable link causes the flexible section of tube to flex and arc.

In a further embodiment, in a relaxed state when substantially no pulling force is applied to the slidable link, the combination of the flexible section of tube and the flexible sheathing form a straight tubular guide. During use of the hand tool, a user squeezes a handle at a proximal end of the hand tool apply a pulling force to the slidable link to control the arc formed by the flexible section of tube to steer a guide wire passing through the hand tool.

In accordance with another embodiment, a straight rigid section of tube can be affixed to a handle of the hand tool. The straight rigid section of tube can be coupled to the combination of the flexible section of tube and the flexible sheathing. In a relaxed state when substantially no pulling force is applied to the slidable link, the combination of the flexible section of tube and the flexible sheathing and the rigid section of tube form a straight tubular region. The handle is configured to control movement of the slidable link along the length of the tubular guide to adjust an arc formed by the flexible section of tube.

In accordance with further embodiments, a first end of the slidable link is affixed to the distal tip of the flexible section of tube. The handle of the hand tool is configured to pull on a second end of the slidable link to control an arc of the flexible section of tube. A portion of the slidable link between the flexible sheathing and the flexible section of tube conforms to a shape of the arc of the flexible section of tube. In other words, a portion of slidable link adjacent to the flexible sheathing and flexible section of tube conforms to a shape of the arc formed by the combination of flexible sheathing and flexible section of tube.

A ring can be disposed at the distal tip of the flexible section of tube. In such an embodiment, the end of the slideable link is attached to the ring disposed at the distal tip.

When a pulling force is applied to the slidable link to adjust an arc of the section of flexible tube, the flexible sheathing prevents the slidable link from bowing away from the flexible section of tube.

In furtherance of preventing bowing of the slidable link away from the flexible section of tube, an inner diameter of the flexible sheathing can be substantially equal to an outer diameter of the flexible section of tube. In such an embodiment, the inner surface of the flexible sheathing forces the slidable link to touch or nearly touch the flexible sheathing when a force is applied to the slidable link.

In accordance with yet further embodiments, the handle is a scissors handle including a first lever and a second lever. The first lever of the scissors handle is fixedly attached to the rigid section of the tubular guide. An end of the slidable link can be affixed to the distal tip of the flexible section of tube. The second lever of the scissors handle pivots about the first lever of the scissors handle. The second end of the slidable link is in communication with the second lever of the scissors handle. For example, movement of the second lever applies a pulling force (or pushing force if the link is rigid) on the slidable link. The slidable link can be configured to slide axially along the length of the tubular guide to adjust the arc based on pivoting of the second lever with respect to the first lever of the handle. A shape of the arc of the tubular guide varies depending on an angular orientation of the first lever with respect to the second lever.

Embodiments herein further include manufacturing or assembly of the hand tool with the flexible tubular tip. For example, in one embodiment, a manufacturer receives a tubular guide including at least a flexible section of tube; attaches an end of a link to a distal tip of the flexible section of tube; and encases the flexible section of tube with a flexible sheathing to dispose or sandwich a length of the link between an outer surface of the flexible section of tube and an inner surface of the flexible sheathing.

Embodiments herein further include use of the hand tool as discussed herein. For example, an operator receives a hand tool, the hand tool includes: a handle, a tubular guide, the tubular guide including a flexible section of tube covered by a flexible sheathing, a slidable link between an outer surface of the flexible section and an inner surface of the flexible sheathing. The operator utilizes the handle of the hand tool to control a force applied to the slidable link to adjust an arc formed by the flexible section of tube. The hand tool as discussed herein is used to steer a guide wire into a hole drilled into a bone. For example, the operator of the hand tool can insert and slide a guide wire through the rigid tube starting at the handle. The operator pushes the guide wire through the rigid tubular portion to and through the flexible section at the distal end of the hand tool. Based on a degree of squeezing the handle during a surgical operation, the operator can adjust the tip at the distal end of the hand tool to steer the end of the guide wire to a desired location such as the hole drilled in a bone.

These and other example embodiments are discussed in more detail below.

As discussed above, techniques herein are well suited for use in steering a guide wire. However, it should be noted that embodiments herein are not limited to use in such applications and that the techniques discussed herein are well suited for other applications as well.

Note that although each of the different features, techniques, configurations, etc., herein may be discussed in different places of this disclosure, it is intended that each of the concepts can be utilized independently of each other or, where suitable, in combination with each other. Accordingly, the one or more present inventions as described herein can be embodied and viewed in many different ways.

Also, note that this preliminary discussion of embodiments herein does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), and additional points of novelty, the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION

According to a first configuration (e.g., FIGS. 1-12), a hand tool is configured to include a shaft, a handle disposed at a proximal end of the shaft, and a tubular tip disposed on a hinge at a distal end of the shaft. The tubular tip pivots about the hinge, providing a way to steer a resource to a specific location in a medical site.

In accordance with a second configuration (e.g., FIGS. 13-20), a hand tool includes a flexible section of tube, a flexible sheathing, and a link. The flexible sheathing encases the flexible section of tube. At least a portion of the link resides between an outer surface of the flexible section of tube and an inner surface of the flexible sheathing. One end of the link is affixed to a distal tip of the flexible section of tube. Pulling on the link causes the flexible section of tube to arc.

Figure 1:
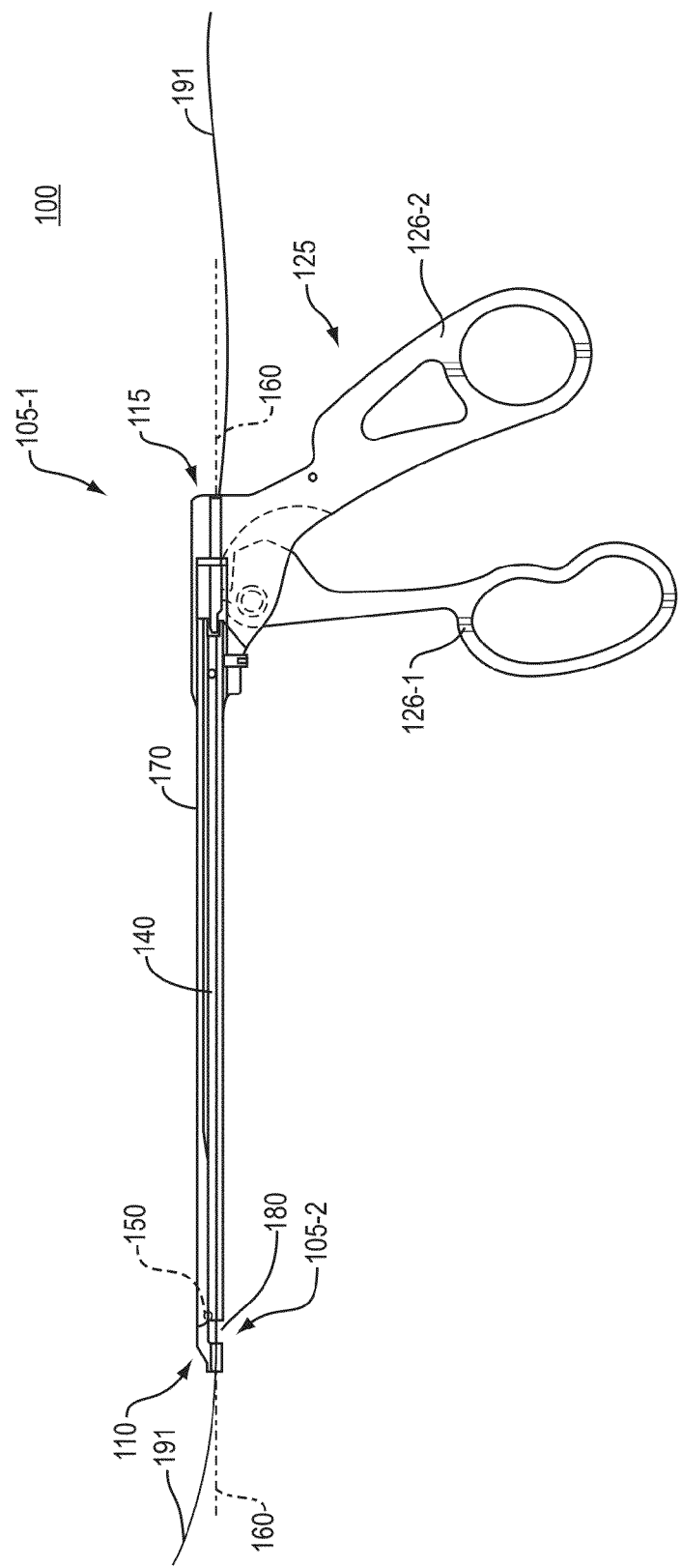
FIG. 1 is an example side view diagram of a hand tool according to embodiments herein.

More specifically, FIG. 1 is an example side view of a hand tool 100 including a tip 110 according to embodiments herein. Tip 110 can include a cannula, bore, tubular region, bore, etc.

In general, a user squeezes a handle 125 at a proximal end of the hand tool 100 to control an angular position of hinged, tip 110 at a distal end 105-2 of the hand tool 100. The hand tool 100 enables a user to steer a resource such as a guide wire passing through tubular guide 115 to a desired location.

More specifically, according to one configuration, the hand tool 100 includes a handle 125 such as a scissors handle, a straight rigid tube along shaft 140, and hinged tip 110. The proximal end 105-1 of the rigid shaft 140 (through which tubular guide 115 passes) is fixedly attached to lever 126-2 of handle 125. The tip 110 is coupled to the shaft 140 via a hinge assembly 150 at distal end 105-2 opposite the handle 125.

In one embodiment, the hinged, tubular tip 110 pivots about the hinge assembly 150 securing the hinged tip 110 to the shaft 140. Similar to the shaft 140, the hinged tip 110 also can include a tubular portion. In such an embodiment, the tubular guide 115 of the hand tool 100 extends along axis 160 from the proximal end 105-1 through the handle 125 and through the distal end of the shaft 140.

The hand tool 100 can include a link 170 extending from the handle 125 to the hinged tip 110. The link 170 can be configured to slide along shaft 140. Squeezing the lever 126-1 with respect to lever 122-2 of handle 125 causes the link 170 to slide axially along the shaft 140.

According to one configuration, the link 170 is in contact with the hinged tip 110 via a lug assembly (FIGS. 4-9) to control actuation of the hinged tip 110. Thus, via squeezing of the lever scissors handle 125 and corresponding axial movement of the link 170, the scissors handle 125 adjusts an angular offset of the tubular hinged tip 110 with respect to axis 160 or rigid tube formed in shaft 140. Depending on a degree of squeezing the lever 126-1 with respect to the lever 126-2 of the scissors handle 125, the link 170 moves and controls the hinged tip 110 to be axially aligned or angularly offset with respect to axis 160. Thus, the tubular portion of the hinged tip 110 can be an extension tube that is axially aligned or angularly offset with respect to axis 160.

Depending on a degree of squeezing the handle 125, the hinged, tubular tip 110 can be angularly offset by different amounts with respect to the axis 160. The hinged, tubular tip 110 acts as a steerable extension of the tubular guide 115 in shaft 140.

Figure 5:
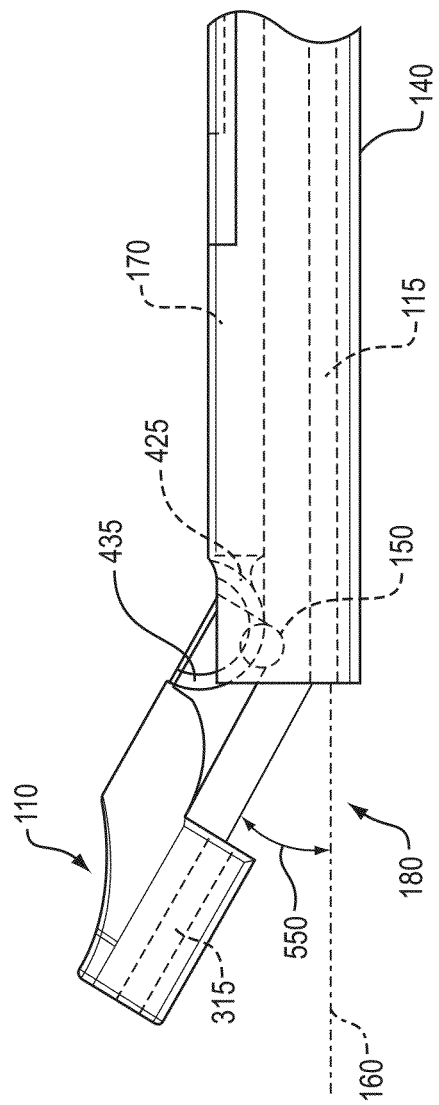
FIG. 5 is an example side view diagram of a hinged, tubular tip in a second position according to embodiments herein.

In one configuration, when the tubular section in the hinged tip 110 is positioned to axially align with the rigid tube formed in shaft 140, there is an open space or gap 180 between the tubular portion in the hinged tip 110 and the end of the rigid tube formed in shaft 140. Thus, there is a gap 180 (e.g., open space) between the tubular portion in the hinged tip 110 and the end of the shaft 140. When the hinged tip 110 is positioned off axis with respect to axis 160 of the rigid tube formed in shaft 140 via squeezing the handle 125, a size of the gap 180 or open space between the end of the rigid tube and the tubular portion of the hinged tip 110 increases (FIG. 5).

By way of a non-limiting example, the hand tool 100 as discussed herein can be used to steer a resource such as a guide wire 191 into a hole drilled into a bone. For example, in one embodiment, the operator of the hand tool 100 inserts and slides a guide wire 191 through the tubular guide 115 starting at the handle 125 and pushes the guide wire 191 towards and through the tubular guide 115 in shaft 115 to the distal end 105-2. The operator also pushes the guide wire 191 to pass through a tubular section formed through tip 110. Based on a degree of squeezing the handle 125 during a surgical operation, the operator can adjust the tip 110 at the distal end 105-2 of the hand tool 100 to steer the end of the guide wire 191 (which passes through the tubular guide 115 in shaft 140 and passes through tubular portion of the tip 110) to a desired location such as the hole drilled in a bone of a medical site.

Figure 2:
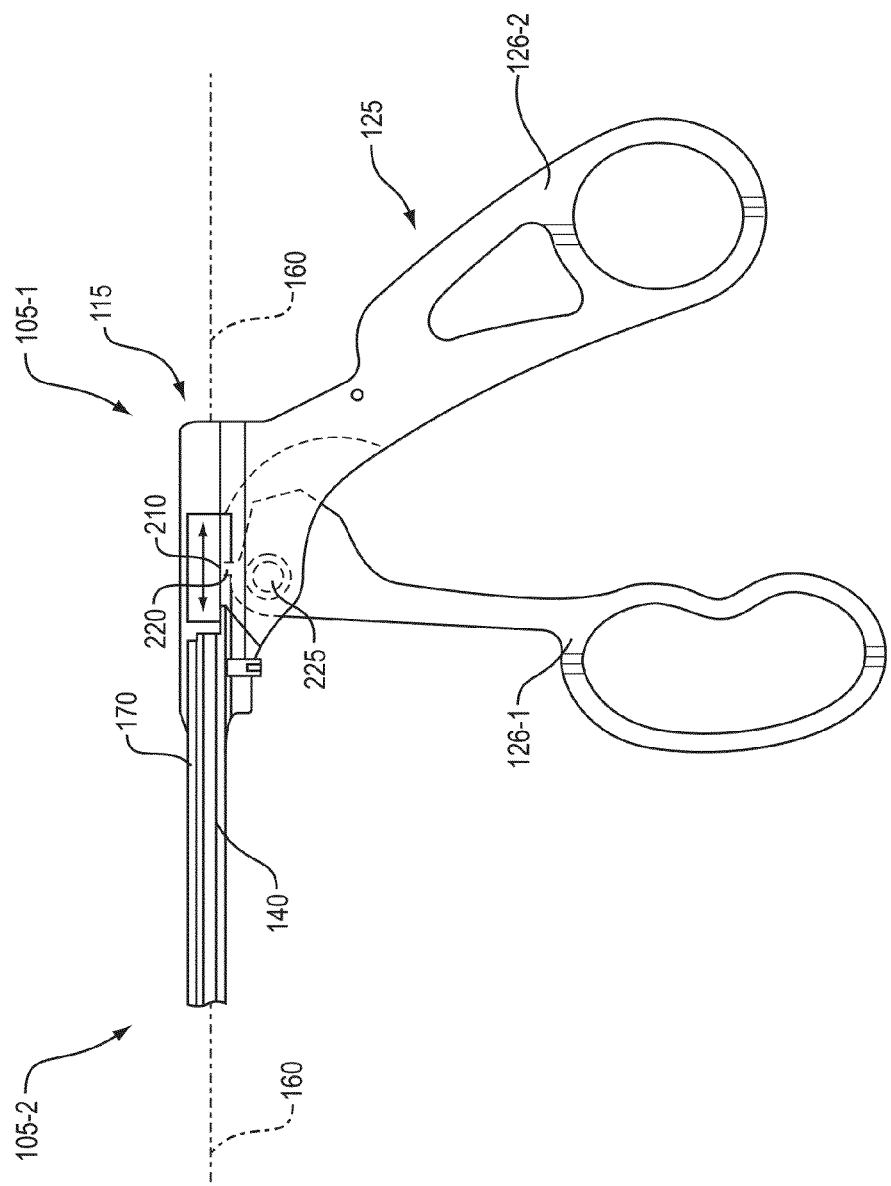
FIG. 2 is an example side view diagram of a hand tool according to embodiments herein.

FIG. 2 is an example side view diagram of hand tool 100 according to embodiments herein. As shown, the shaft 140 is fixedly attached to the lever 126-2 of handle 125. Lever 126-1 rotates about pivot 225.

Projection 220 of lever 126-1 resides in notch 210 formed in link 170. Accordingly, when the user squeezes the lever 126-1 towards lever 126-2, the link 170 slides parallel to axis 160 towards a distal end 105-2 of the shaft 140. Conversely, when the user moves the lever 126-1 away from lever 126-2, the link 170 slides parallel to axis 160 towards the proximal end 105-1 of the hand tool 100.

Figure 3:
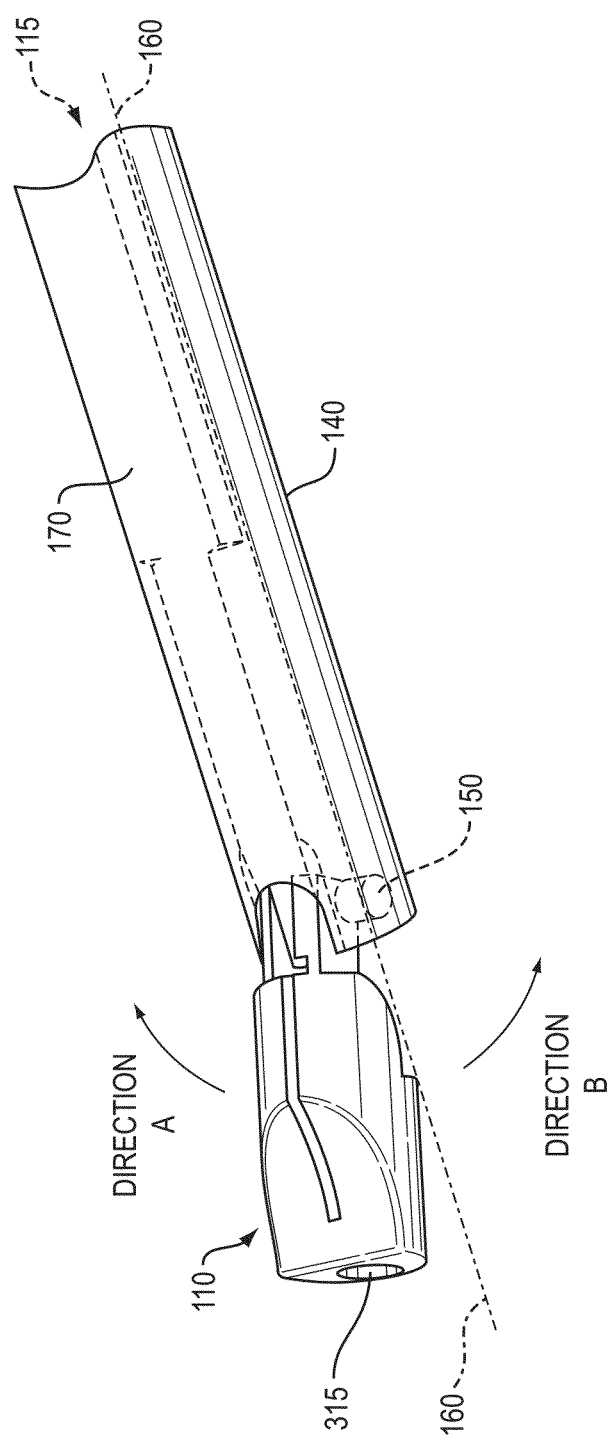
FIG. 3 is an example perspective view diagram of a hinged tubular tip of a hand tool according to embodiments herein.

FIG. 3 is an example perspective view diagram of a hinged tubular tip 110 according to embodiments herein. As shown, shaft includes tubular guide 115; tip 110 includes tubular guide 315. Movement of link 170 along axis 160 (via squeezing of handle 125 as previously discussed) causes the hinged, tubular tip 110 to rotate about the hinge assembly 150 as shown. For example, when the user squeezes the lever 126-1 towards lever 126-2 as previously discussed, the link 170 slides parallel to axis 160 towards a distal end 105-2 of the shaft 140, which causes the tip 110 to rotate about the hinge assembly 150 in direction B. Conversely, when the user moves the lever 126-1 away from lever 126-2, the link 170 slides parallel to axis 160 towards the proximal end 105-1 of the hand tool 100, which causes the tip 110 to rotate about the hinge assembly 150 in direction A.

Figure 4:
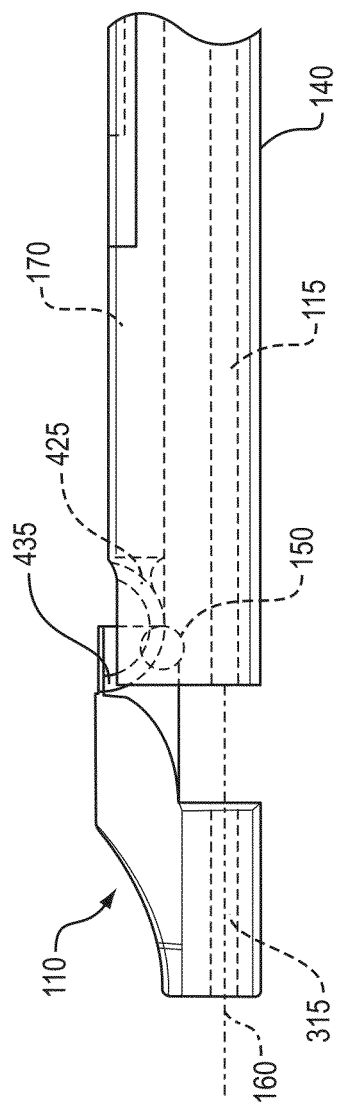
FIG. 4 is an example side view diagram of a hinged, tubular tip in a first position according to embodiments herein.

FIG. 4 is an example side view diagram of a hinged, tubular tip in a first position according to embodiments herein. As shown, link 170 includes curved lug 425. Tip 110 includes a lug channel 435. The curved lug 425 of link 170 matably fits and slides into the lug channel 435 of the tip 110. Movement of the curved lug 425 controls an angular position of the tip depending on a position of the link 170 along shaft 140. In the position as shown in FIG. 4, the tubular guide 315 formed in the tip 110 is axially aligned (on axis 160) with the tubular guide 115 of shaft 140.

FIG. 5 is an example side view diagram of a hinged, tubular tip in a second position according to embodiments herein. As previously discussed, link 170 includes curved lug 425. Tip 315 includes a lug channel 435. The curved lug 425 of link 170 slidably fits into the lug channel of the tip 110. Movement of the link 170 and thus curved lug towards the handle 125 or proximal end 105-1 of hand tool 100 causes the tip 110 to rotate clockwise around hinge assembly 150 as shown to offset the tubular guide 315 at an increased angle 550 with respect to the tubular guide 115.

Figure 6:
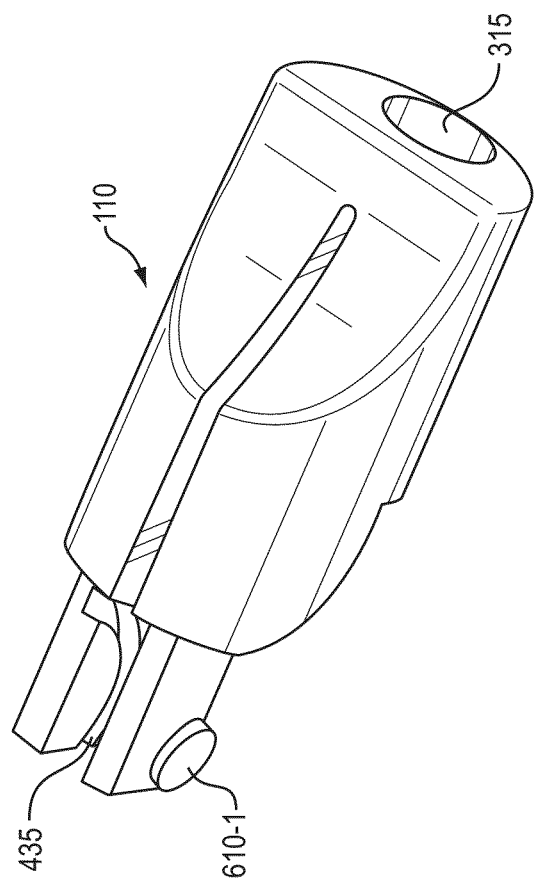
FIG. 6 is an example perspective view diagram of a tubular tip of a hand tool according to embodiments herein.

FIG. 6 is an example perspective view diagram of a tubular tip 110 of a hand tool 100 according to embodiments herein. As shown, the tip 110 includes lug channel 435, tubular guide 315, and projection 610-1. Projection 610-1 is part of hinge assembly 150 and matably attaches to respective dimples formed at the distal end 105-2 of shaft 140 such that the tip rotates as previously discussed.

Figure 7:
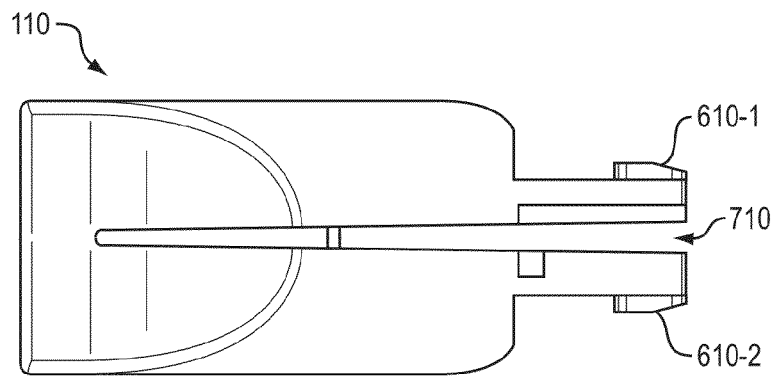
FIG. 7 is an example diagram illustrating a top view of a tubular tip according to embodiments herein.

FIG. 7 is an example diagram illustrating a top view diagram of a tubular tip 110 according to embodiments herein. As shown, the tip 110 includes projection 610-1 and projection 610-2, which form part of hinge assembly 150. The tip 110 can include a spacing 710 to press and subsequently mate projections 610 of hinge assembly 150 into respective dimples formed at the distal end 105-2 of the shaft 140.

Figure 8:
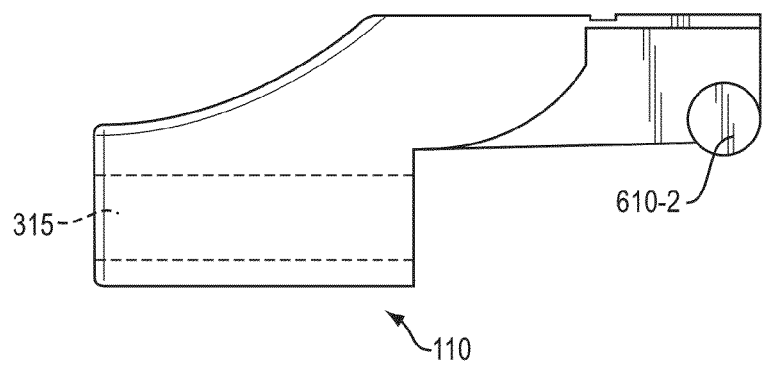
FIG. 8 is an example diagram illustrating a side view of a tubular tip according to embodiments herein.

FIG. 8 is an example diagram illustrating a side view of a tubular tip 110 according to embodiments herein.

Figure 9:
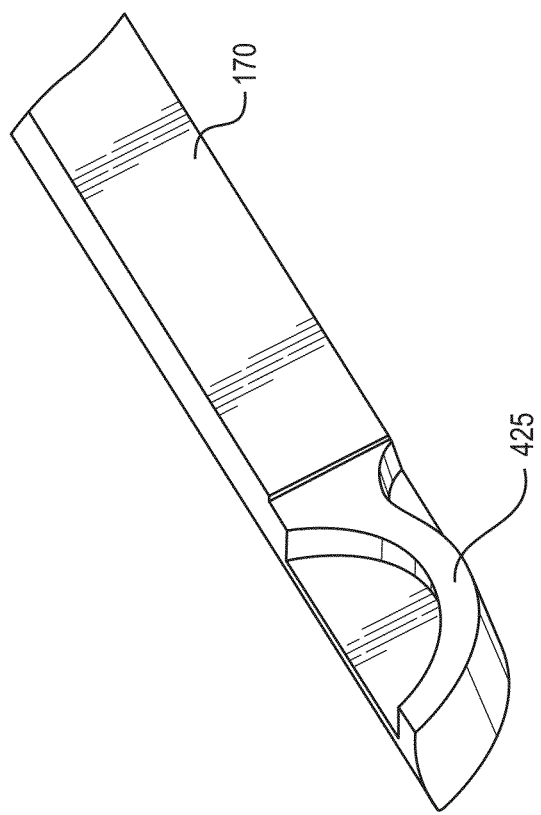
FIG. 9 is an example perspective diagram illustrating a tip of a link according to embodiments herein.

FIG. 9 is an example perspective diagram illustrating a tip region of link 170 according to embodiments herein. As shown, and as previously discussed, the distal end of link 170 can include a curved lug 425 to control an angular orientation of the hinged, tubular tip 110 at the distal end 105-2 of the hand tool 100.

Figure 10:
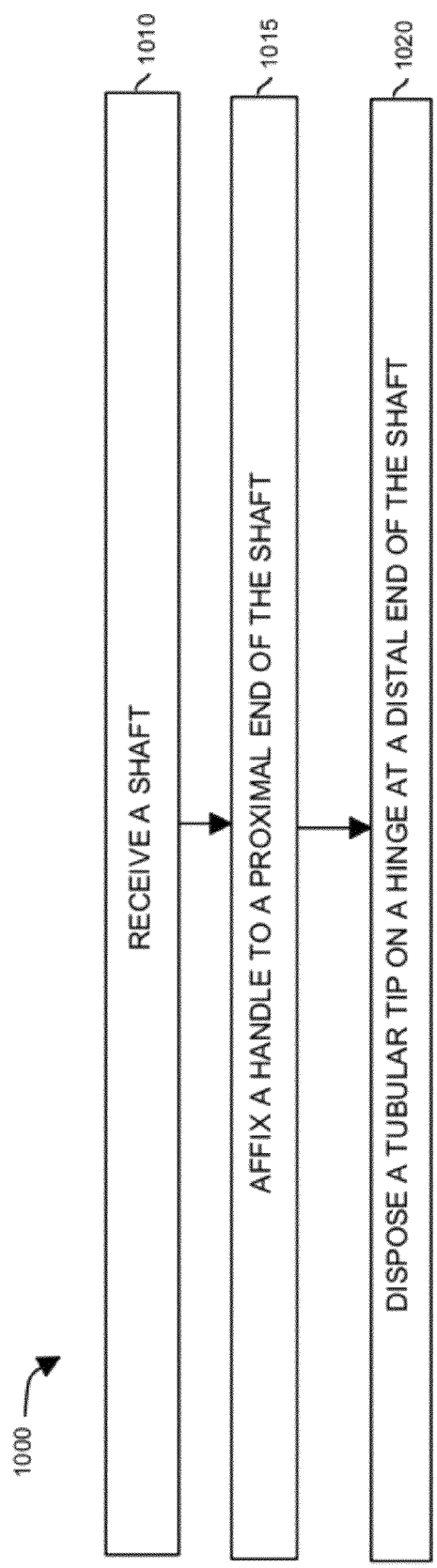
FIG. 10 is a flowchart illustrating an example method of manufacturing a hand tool according to embodiments herein.

FIG. 10 is a flowchart 1000 illustrating an example method of manufacturing or assembling a hand tool 100 having a hinged, tubular tip 110 according to embodiments herein. Note that the order of steps is shown by way of non-limiting example only and that the steps can be performed in any suitable order.

In step 1010, a hand tool assembler (e.g., manufacturer, designer, fabricator, etc.) receives a shaft 140.

In step 1020, the hand tool assembler affixes a handle 125 to a proximal end 105-1 of the shaft 140.

In step 1030, the hand tool assembler disposes a tubular tip 110 on a hinge assembly 150 at a distal end 105-2 of the shaft 140.

Figure 11:
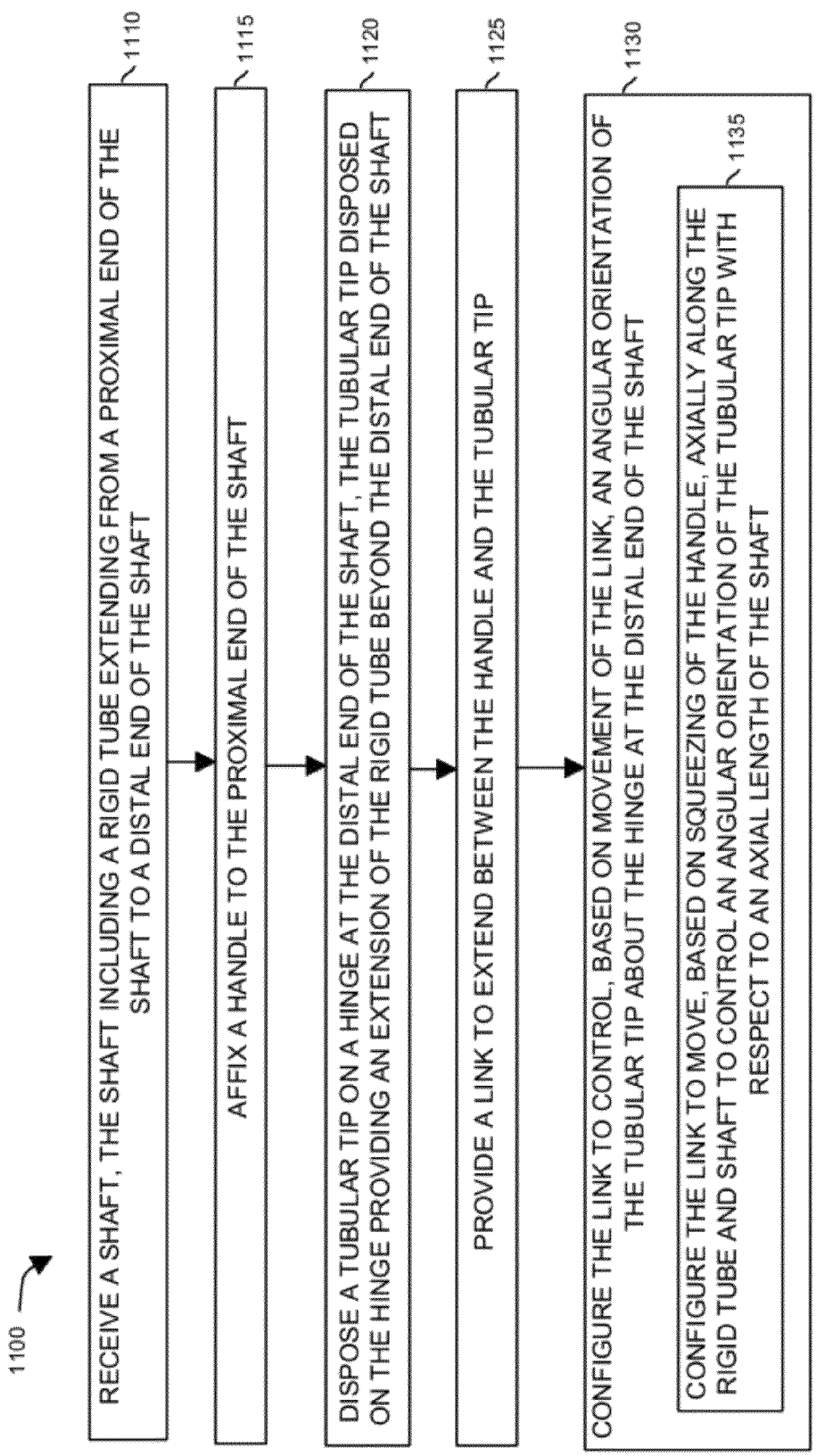
FIG. 11 is a flowchart illustrating an example method of manufacturing a hand tool according to embodiments herein.

FIG. 11 is a flowchart 1100 illustrating an example method of manufacturing a hand tool 100 according to embodiments herein.

In step 1110, an assembler receives a shaft 140. The shaft 140 can include or be a rigid tube extending from a proximal end 105-1 of the shaft 140 to a distal end 105-2 of the shaft 140.

In step 1115, the assembler affixes a handle 125 to the proximal end 105-1 of the shaft 140.

In step 1120, the assembler disposes a tubular tip 110 on a hinge assembly 150 at the distal end 105-2 of the shaft 140.

The tip 110 disposed on the hinge assembly 150 provides an extension of the rigid tubular guide 115 beyond the distal end 105-2 of the shaft 140.

In step 1125, the assembler provides a link 170 to extend between the handle 125 and the tubular tip 110.

In step 1130, the assembler configures the link 170 to control, based on movement of the link 170, an angular orientation of the tubular tip 110 about the hinge assembly 150 at the distal end 105-2 of the shaft 140.

In sub-step 1135, the assembler configures the link 170 to move, based on squeezing of the handle 125, axially along the tubular guide 115 in the shaft 140 to control an angular orientation of the tubular tip 110 with respect to an axial length of the shaft 140.

Figure 12:
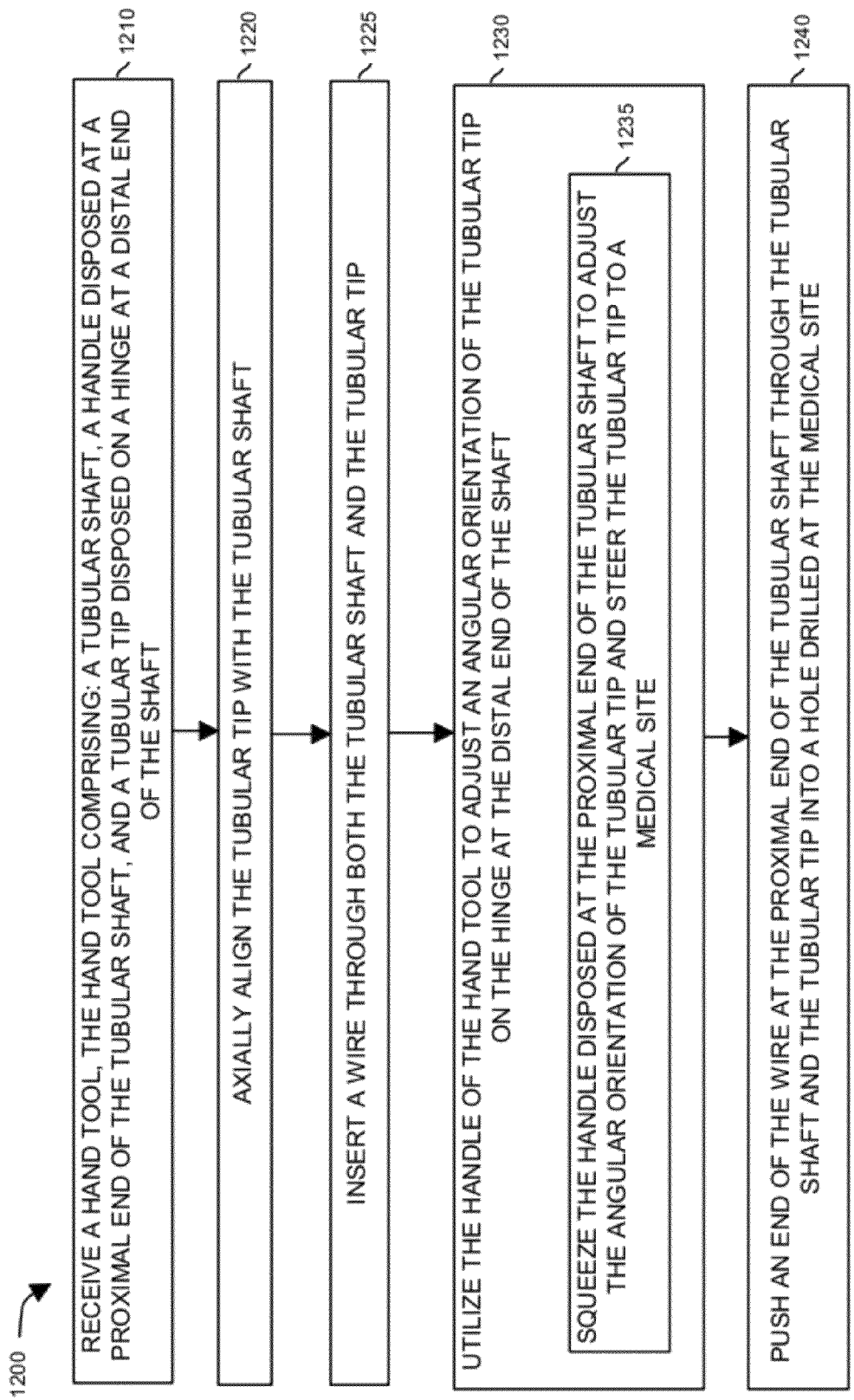
FIG. 12 is a flowchart illustrating example steps of a user utilizing a hand tool having a hinged, tubular tip according to embodiments herein.

FIG. 12 is a flowchart illustrating example steps of a user utilizing a hand tool having a hinged, tubular tip according to embodiments herein.

In step 1210, a user (e.g., a surgeon, operator, etc.) receives a hand tool 100. The hand tool 100 comprises: a shaft 140 having tubular guide 115, a handle 125 disposed at a proximal end 105-1 of the shaft 140, and a tubular tip 110 disposed on a hinge assembly 150 at a distal end 105-2 of the shaft 140.

In step 1220, via the handle 125, the user axially aligns the tubular tip 110 with the shaft 140.

In step 1225, the user inserts a wire through both the tubular guide 115 through shaft 140 and the tubular tip 110.

In step 1230, the user utilizes the handle 125 of the hand tool 100 to adjust an angular orientation of the tubular tip 110 on the hinge assembly 150 at the distal end 105-2 of the shaft 140.

In sub-step 1235, the user squeezes the handle 125 disposed at the proximal end 105-1 to adjust the angular orientation of the tip 110 and steer the tubular guide 315 in tip 110 to a medical site.

In step 1240, the user pushes an end of the wire at the proximal end 105-1 of the tubular guide 115 in the tubular guide 115 of the shaft 140 through the tubular guide 315 and the tubular tip 110 into a hole drilled at the medical site.

Figure 13:
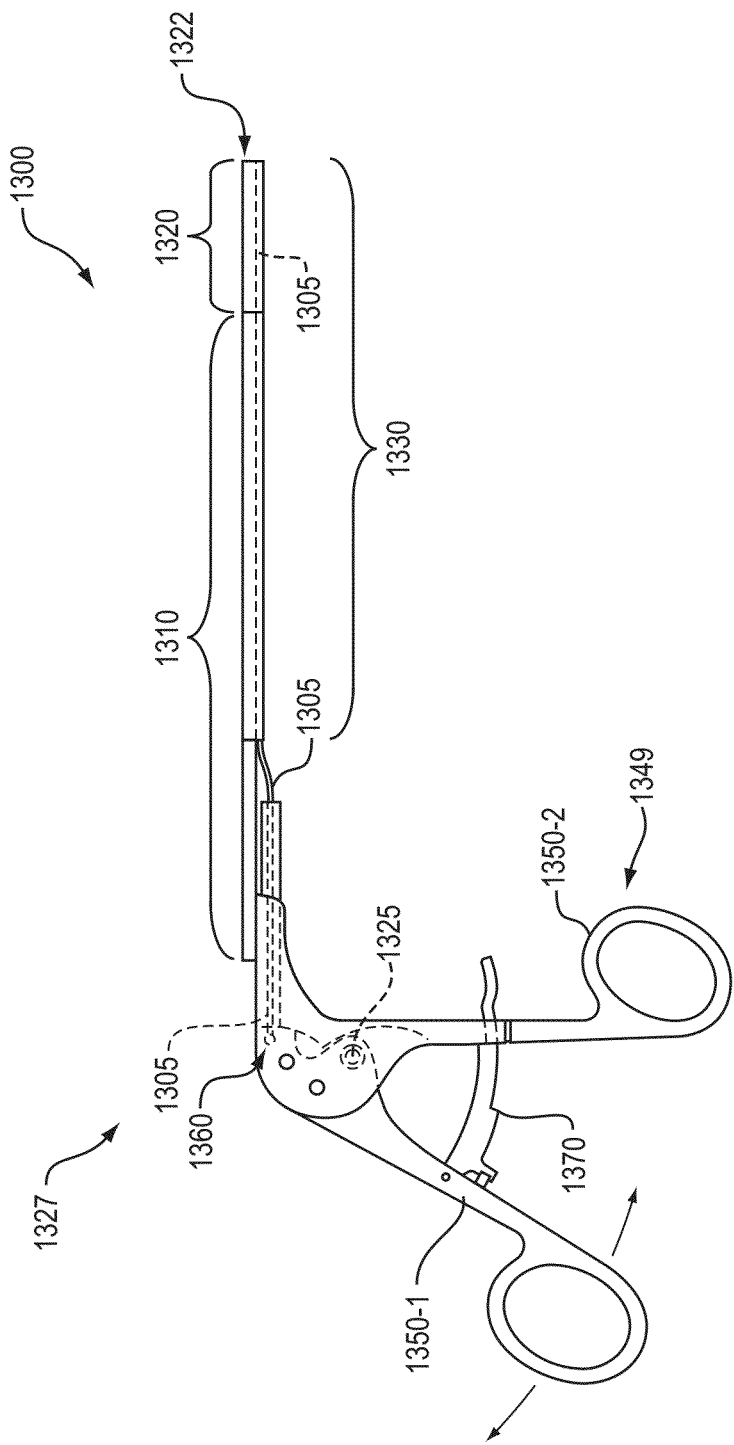
FIG. 13 is an example side view diagram of a hand tool according to embodiments herein.

FIG. 13 is an example side view diagram of a hand tool 1300 according to embodiments herein.

Further embodiments herein include a hand tool 1300 such as a cannulated steerable guide used in surgical applications. In general, a user operates a handle 1349 at a proximal end 1327 of the hand tool 1300 to control movement of a flexible tip at a distal end 1322 of the hand tool 1300.

By way of a non-limiting example, the hand tool 1300 can be configured to include a scissors handle including lever 1350-1 and lever 1350-2. The hand tool 1300 can further include a rigid section of tube 1310, a flexible section of tube 1320 (e.g., a coil tube, plastic tube, etc.), a flexible sheathing 1330, and a link 1305 (e.g., wire, cable, strand, string, etc.). In one embodiment, the rigid section of tube 1310 is a straight piece of stainless steel tube.

The lever 1350-1 rotates about pivot 1325 with respect to lever 1350-2 of handle 1349. One end of the rigid section of tube 1310 is fixedly attached to the lever 1350-2 of the handle 1349. The flexible section of tube 1320 is fixedly attached to an end of the rigid section of tube 1310 to form an extension. For example, a combination of the rigid section of tube 1310 and flexible section of tube 1320 form a single tube having a rigid portion at one end (e.g., towards the handle end or proximal end 1327) and a flexible portion at the distal end 1322. The combination of rigid section of tube 1310 and the flexible section of tube 1320 accept passage of a resource such as a guide wire used in surgery.

One end of the link 1305 in the hand tool 1300 is fixedly attached to a distal end 1322 of the flexible section of tube 1320; the other end of the link 1305 is fixedly attached to lever 1350-1 at link connection 1360.

In one embodiment, the link 1305 resides adjacent to and on an underside of the rigid section of tube 1310 and the flexible section of tube 1320. The flexible sheathing 1330 is pulled over the flexible section of tube 1305 and at least a portion of the rigid section of tube 1310 as shown.

In accordance with further embodiments, the flexible sheathing 1330 acts as a sleeve covering the flexible section of tube 1320 and at least a portion of the rigid section of tube 1310. The link 1305 slides along the combination of the rigid section of tube 1310 and flexible section of tube 1320 when the lever 1350-1 is squeezed. When the lever 1350-1 is moved in a direction towards lever 1350-2 via squeezing, the lever 1350-1 applies a force on link 1305 causing the flexible section of tube 1320 to form an arc.

In one embodiment, the handle 1349 includes a tab 1370 to prevent movement of lever 1350-1 with respect to lever 1350-2.

Figure 14:
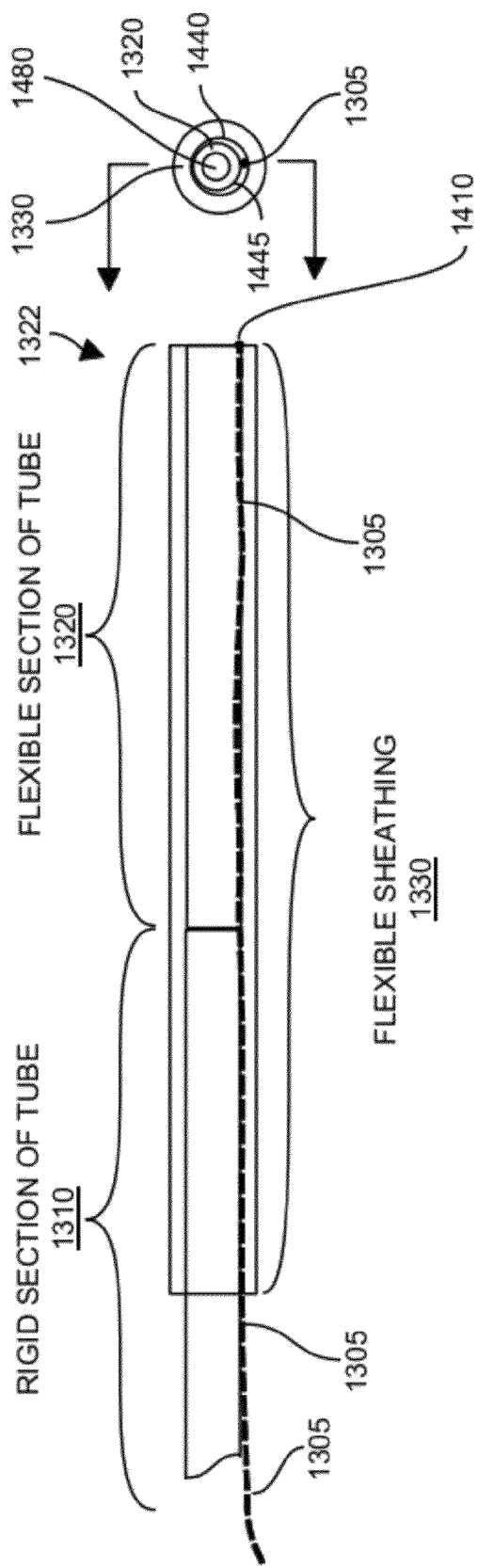
FIG. 14 is an example side view diagram of a tubular guide in a hand tool according to embodiments herein.

FIG. 14 is an example side view diagram of a tubular guide according to embodiments herein.

As shown, the inner diameter of the flexible sheathing 1330 is approximately the same diameter as an outer diameter of the flexible section of tube 1320. The link 1305 resides between the inner surface 1440 of the flexible sheathing 1330 and outer surface 1445 of the flexible section of tube 1320. The end of the link 1305 connects to the flexible section of tube 1320 via link connection 1410 (e.g., weld, solder, glue, adhesive, etc.) at distal end 1322.

By way of a non-limiting example, in one embodiment, the flexible section of tube 1320 and link 1305 are made from a metallic material. The flexible sheathing can be made from any suitable pliable material such as plastic, metal, etc.

In accordance with further embodiments, the inner bore of the rigid section of flexible tube 1310 and the flexible section of tube 1320 form tubular guide 1480 extending from and through the proximal end 1327 of hand tool 1300 to and through the distal end 1322 of the hand tool 1300.

Figure 15:
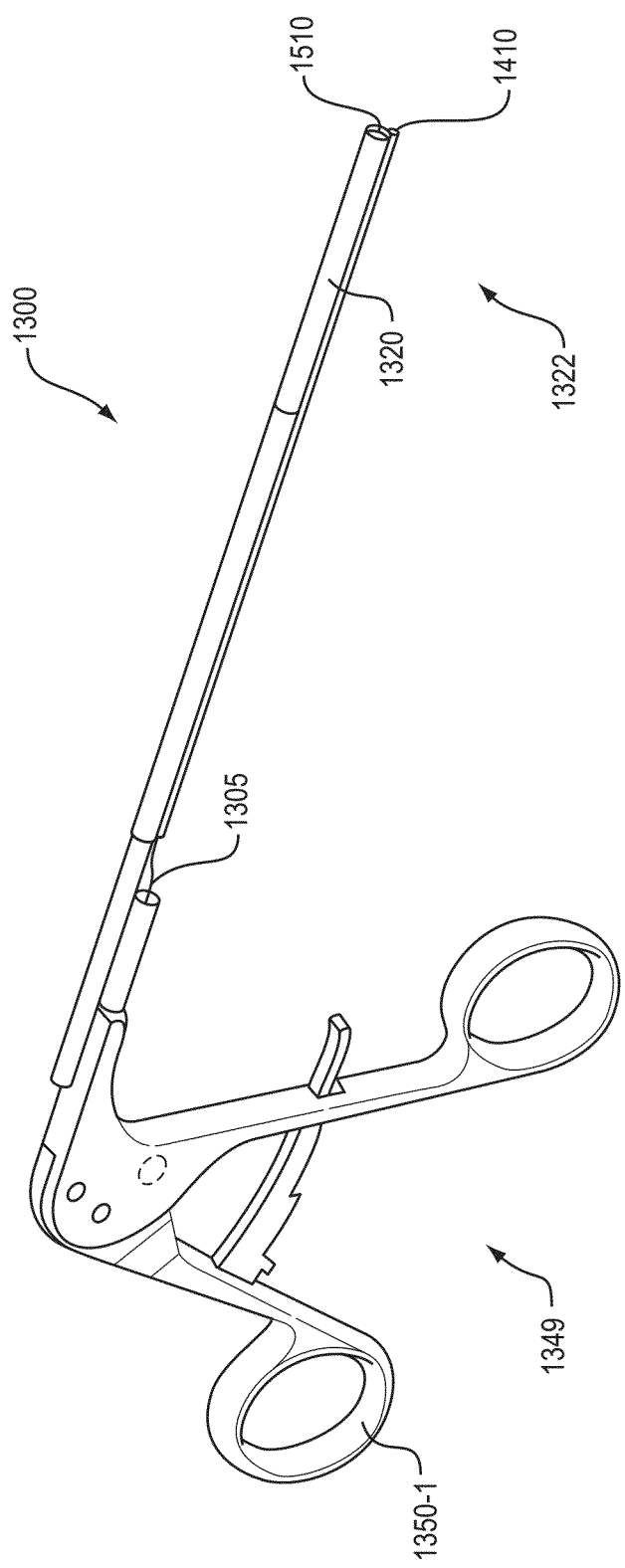
FIG. 15 is an example perspective view diagram of a hand tool according to embodiments herein.

FIG. 15 is an example perspective view diagram of hand tool 1300 according to embodiments herein. As shown, the hand tool 1300 can include a distal ring 1510 disposed at distal end 1322 of flexible section of tube 1320 of hand tool 1300. The distal ring 1510 provides a location in which to form link connection 1410 between the end of link 1305 and end of the flexible section of tube 1320 at the distal end 1322.

Figure 16:
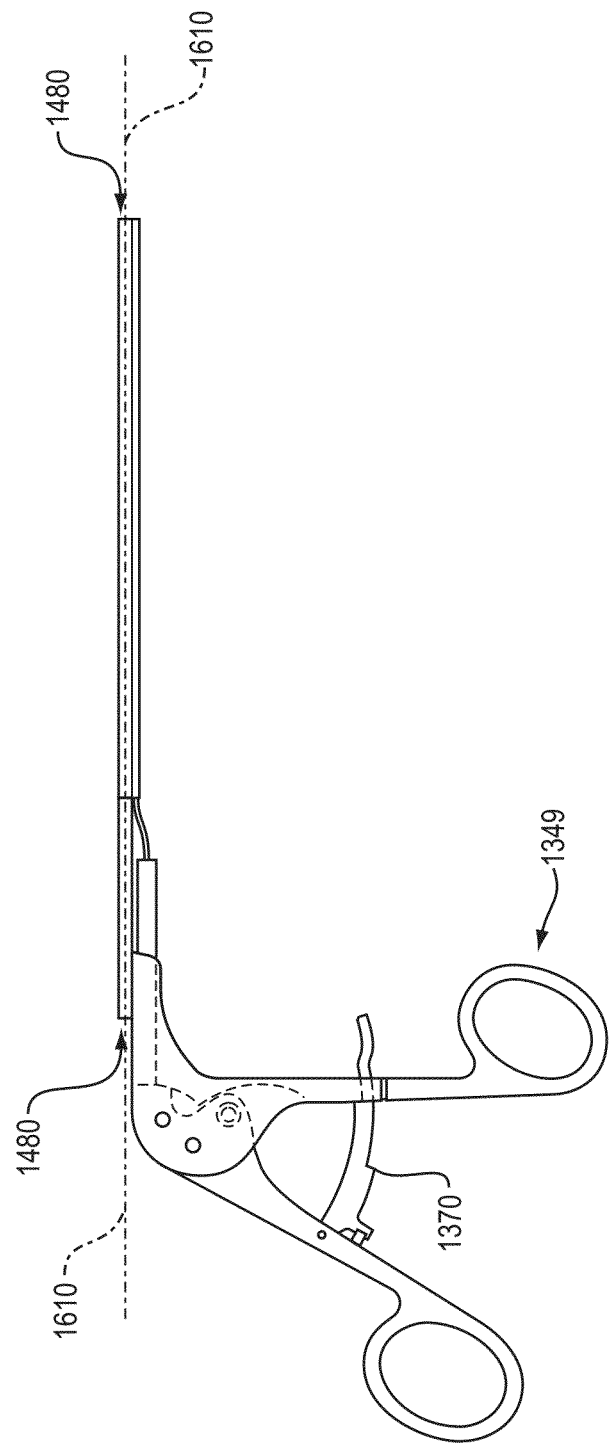
FIG. 16 is an example side view diagram of a hand tool and corresponding flexible, tubular tip in a first position according to embodiments herein.

FIG. 16 is an example side view diagram of a hand tool 1300 and corresponding flexible, tubular tip in a first position according to embodiments herein.

When the handle 1349 is not squeezed and in a first position as shown in FIG. 16, the rigid section of tube 1310 and the flexible section of tube 1320 align along an axis 1610 to form a substantially straight tubular guide 1480.

Figure 17:
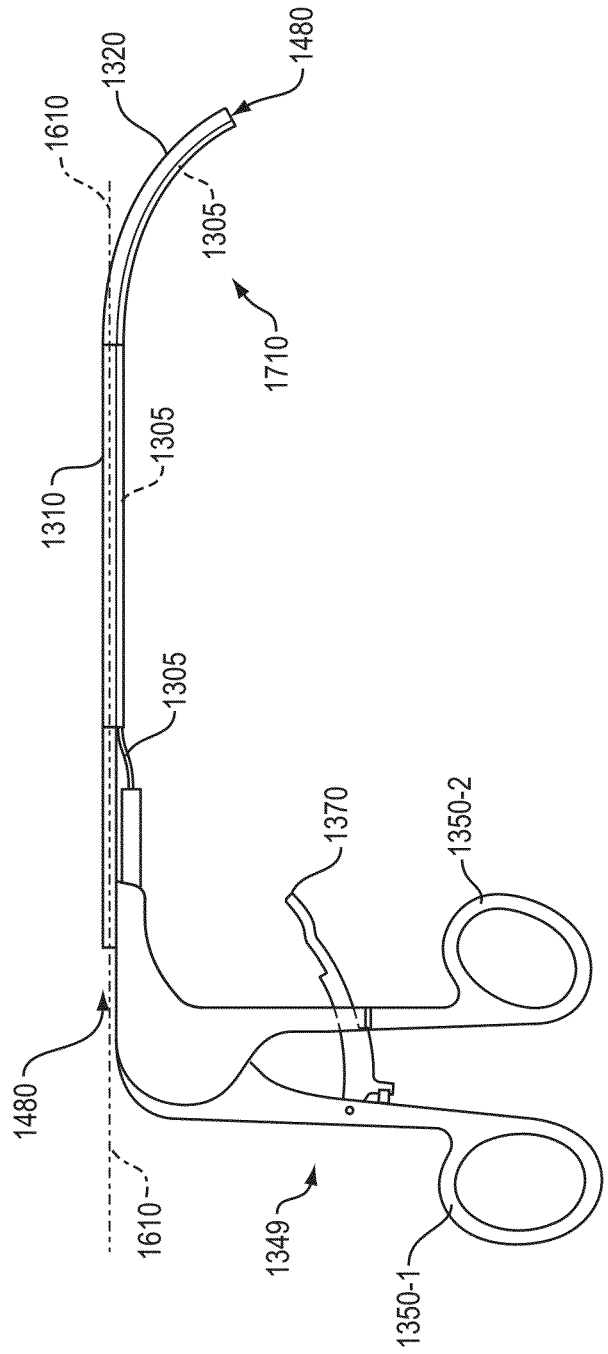
FIG. 17 is an example side view diagram of a hand tool and corresponding flexible, tubular tip in a second position according to embodiments herein.

FIG. 17 is an example side view diagram of a hand tool 1300 and corresponding flexible, tubular tip in a second position according to embodiments herein.

Squeezing of the handle 1349 causes the lever 1350-1 to move in a direction towards lever 1350-2. This causes the lever 1350-1 to pull on the link 1305 away from the distal end 1322. The force of pulling on the link 1305 causes the distal end 1322 of the tubular guide 1480 to flex into an arc 1710 as shown (as opposed to being substantially straight in as shown in FIG. 16).

A curvature of the arc 1710 of the flexible section of tube 1320 at the distal end 1322 of the tubular guide 1480 varies depending on how firmly the lever 1350-1 is squeezed with respect to lever 1350-2. During a time of squeezing the lever 1350-1, as shown, the outer flexible sheathing 1330 pulled over the flexible section of tube 1320 at the distal end 1322 prevents the link 1305 from bowing away from the flexible section of tube 1320.

One example use of the cannulated steerable guide (e.g., hand tool 1300) as discussed herein is to steer a guide wire to a desired location. For example, the tube formed by the rigid section of tube 1310 and the flexible section of tube 1320 is opened at both ends. During use, the operator inserts and slides a guide wire through the tubular guide 1480 from the proximal end 1327 towards and through the distal end 1322 of the tubular guide 1480. Based on a firmness of squeezing the handle 1349 and respective levers 1350, the operator can steer the end of the guide wire passing through the tubular guide 1480 to a desired location such a hole drilled though a bone in a medical application.

Figure 18:
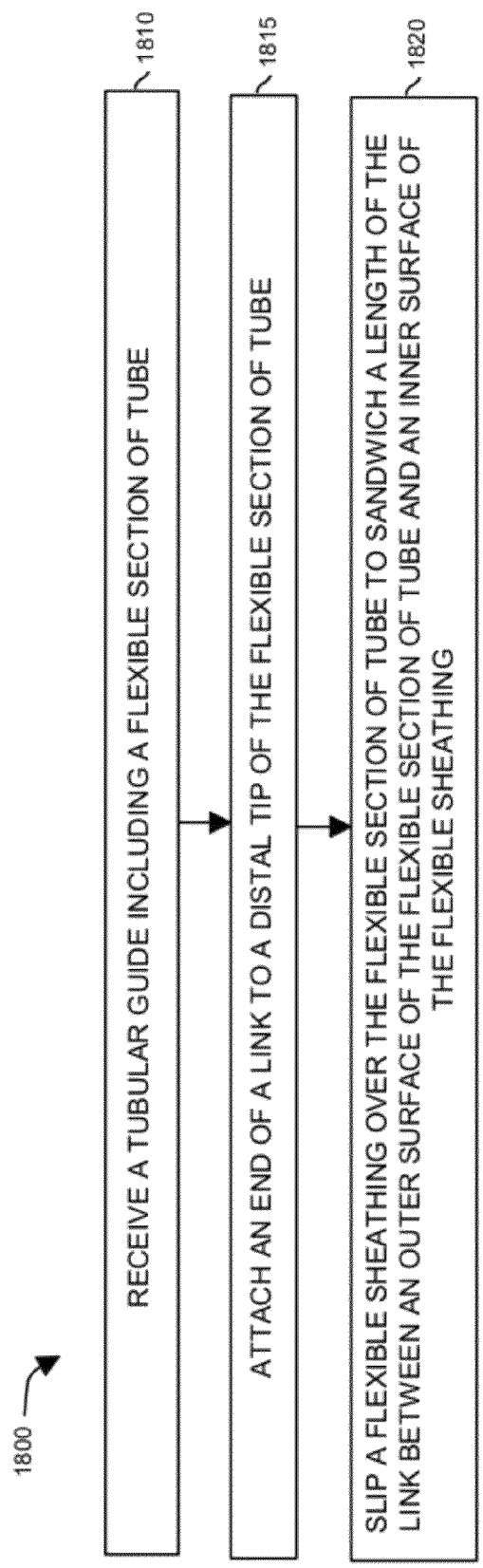
FIG. 18 is a flowchart illustrating an example method of manufacturing a hand tool having a corresponding flexible tubular tip according to embodiments herein.

FIG. 18 is a flowchart 1800 illustrating an example method of manufacturing a hand tool 1300 having a corresponding flexible tubular tip according to embodiments herein.

In step 1810, a hand tool assembler receives a tubular guide 1480 including a flexible section of tube 1320.

In step 1815, the hand tool assembler attaches an end of a link 1305 to a distal end 1322 or tip of the flexible section of tube 1320.

In step 1820, the hand tool assembler slips or positions a flexible sheathing 1330 over the flexible section of tube 1320 to sandwich a length of the link 1305 between an outer surface 1445 of the flexible section of tube 1320 and an inner surface 1440 of the flexible sheathing 1330.

Figure 19:
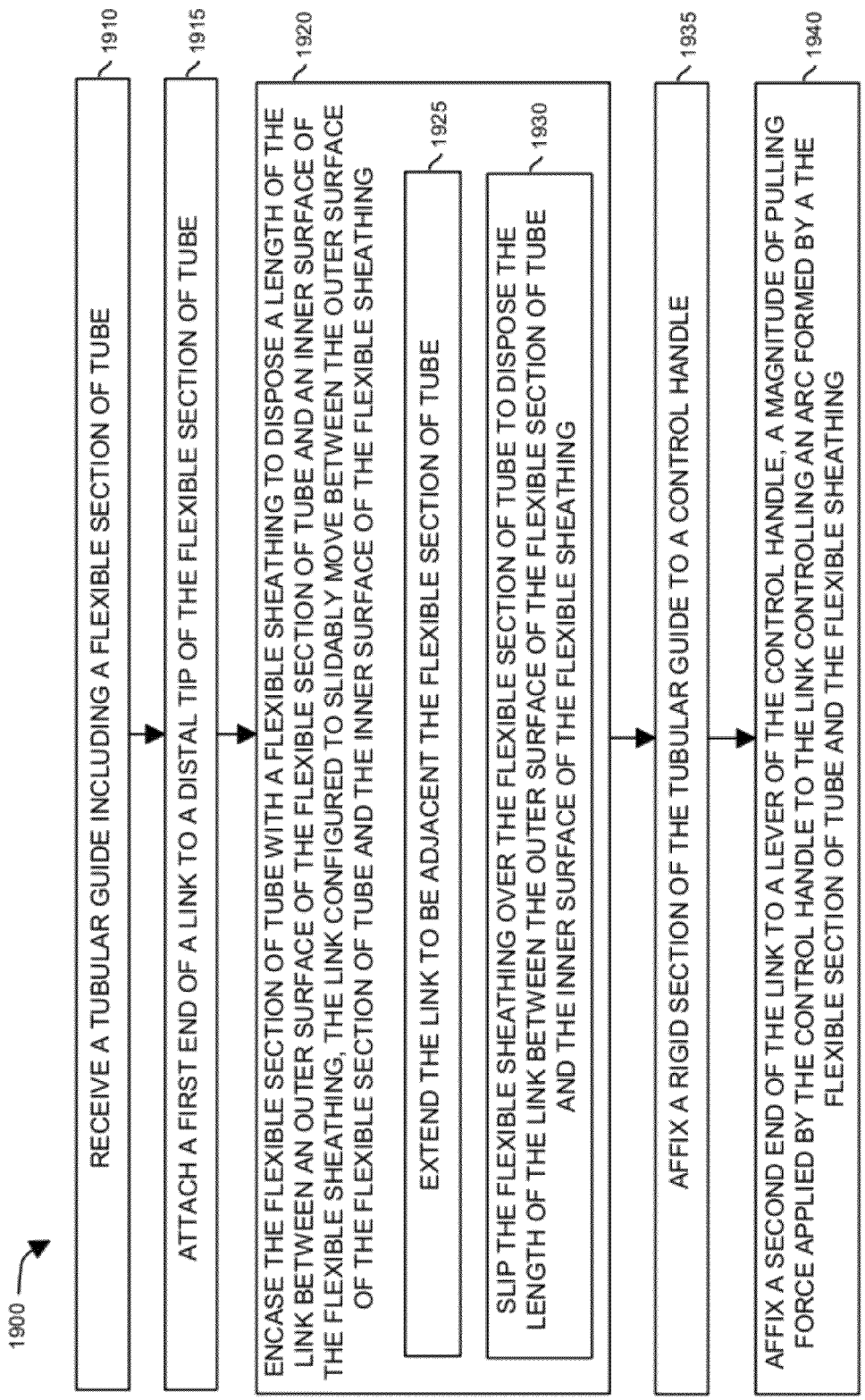
FIG. 19 is a flowchart illustrating an example method of manufacturing a hand tool having a corresponding flexible tubular tip according to embodiments herein.

FIG. 19 is a flowchart 1900 illustrating an example method of manufacturing a hand tool 1300 having a corresponding flexible tubular tip according to embodiments herein.

In step 1910, a hand tool assembler receives a tubular guide 1480 including a flexible section of tube 1320.

In step 1915, the hand tool assembler attaches a first end of the link 1305 to a distal end 1322 of the flexible section of tube 1320 via link connection 1410.

In step 1920, the hand tool assembler encases the flexible section of tube 1320 with a flexible sheathing 1330 to dispose a length of the link 1305 between an outer surface 1445 of the flexible section of tube 1320 and an inner surface 1440 of the flexible sheathing 1330. The link 1305 is configured to slidably move between the outer surface 1445 of the flexible section of tube 1320 and the inner surface 1445 of the flexible sheathing 1330.

In sub-step 1925, the hand tool assembler extends the link 1305 to be adjacent to the flexible section of tube 1320.

In sub-step 1930, the hand tool assembler slips the flexible sheathing 1330 over the flexible section of tube 1320 to dispose the length of the link 1305 between the outer surface 1445 of the flexible section of tube 1320 and the inner surface 1440 of the flexible sheathing 1330.

In step 1935, the hand tool assembler affixes the rigid section of tube 1310 of the tubular guide 1480 to a control handle such as handle 1349.

In step 1940, via link connection 1360 (e.g., screw, weld, etc.), the hand tool assembler affixes a second end of the link 1305 to a lever 1350-1 of the control handle. A magnitude of pulling force applied by the control handle to the link 1305 controls an arc formed by a combination of the flexible section of tube 1320 and the flexible sheathing 1330.

Figure 20:
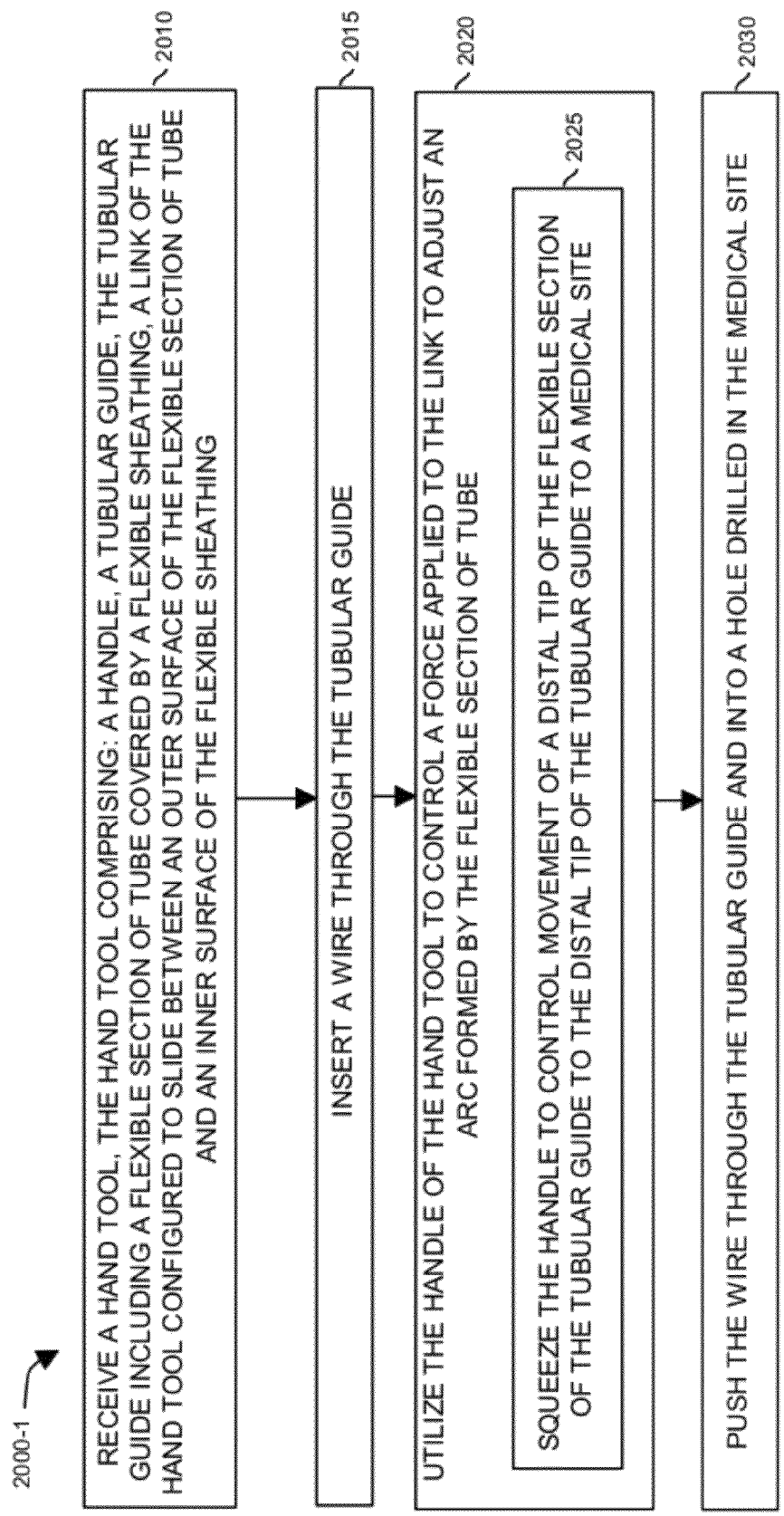
FIG. 20 is a flowchart illustrating example steps of a user utilizing a hand tool having a flexible tip according to embodiments herein.

FIG. 20 is a flowchart 2000 illustrating example steps of a user utilizing a hand tool having a flexible tip according to embodiments herein.

In step 2010, a user receives a hand tool 1300. The hand tool 1300 comprises: a handle 1349, a tubular guide 1480, the tubular guide 1480 including a flexible section of tube 1320 covered by a flexible sheathing 1330, a link 1305 of the hand tool 1349 configured to slide between an outer surface 1445 of the flexible section of tube 1320 and an inner surface 1440 of the flexible sheathing 1330.

In step 2015, a user inserts a resource such as a wire through the tubular guide 1480 of hand tool 1300.

In step 2020, a user utilizes the handle 1349 of the hand tool 1300 to control a force applied to the link 1305 to adjust an arc 1710 formed by the flexible section of tube 1320.

In step 2025, a user squeezes the handle 1349 to control movement of a distal tip and arc 1710 of the flexible section of tube 1320 in the tubular guide 1480 to a medical site.

In step 2030, a user pushes the wire through the tubular guide 1480 and into a hole drilled in the medical site.

Note again that techniques herein are well suited for use in guide applications. However, it should be noted that embodiments herein are not limited to use in such applications and that the techniques discussed herein are well suited for other applications as well.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. A hand tool comprising:
   a shaft;
   a handle disposed at a proximal end of the shaft, the proximal end of the shaft including an opening in which to pass a wire inserted by a user operating the hand tool through the shaft; and
   a tubular tip disposed on a hinge at a distal end of the shaft, the tubular tip receiving the wire passing through the shaft, an angular orientation of the tubular tip adjustable on the hinge to steer the wire to a medical site;
   a slidable link extending between the handle and the tubular tip, squeezing of the handle causing the slidable link to move axially along the shaft to control the angular orientation of the tubular tip with respect to an axis of the shaft;
   wherein the medical site is a hole in a bone;
   wherein an end of the wire disposed at the proximal and of the shaft is pushed into the hole by the user; and
   wherein the tubular tip includes a lug channel in which to receive a lug disposed on a distal end of the slidable link, a length of the lug being curved, the length of the lug sliding within the lug channel to adjust the angular orientation of the tubular tip with respect to the shaft.

2. The hand tool as in claim 1, wherein
   the tubular tip including a first axial end and a second axial end, the first axial end disposed on the tubular tip nearer the hinge than the second axial end, the second axial end being located at a distal end of the hand tool; and
   wherein the first axial end receives the wire, the wire extending through the tubular tip and extending outward beyond the second axial end of the tubular tip, the angular orientation of the tubular tip steering the wire to the medical site.

3. The hand tool as in claim 1, wherein the opening at the proximal end of the shaft is a first opening;
   wherein the shaft includes a second opening at the distal end of the shaft; and
   wherein the shaft is rigid and includes a tubular guide therein, the tubular guide extending through the shaft from the proximal end of the shaft to the distal end of the shaft, the tubular guide receiving and passing the wire to the tubular tip, the wire extending from the first opening through the tubular guide and through the tubular tip to the medical site, the tubular tip on the hinge extending beyond the distal end of the shaft.

4. The hand tool as in claim 2, wherein the handle is a scissors handle including a first lever and a second lever;
   wherein the first lever of the scissors handle is fixedly attached to the shaft; and
   wherein the second lever of the scissors handle pivots about the first lever of the scissors handle, the second lever of the scissors handle in communication with the slidable link, the slidable link configured to slide axially along a length of the shaft and adjust the angular orientation of the tubular tip based on pivoting the second lever with respect to the first lever of the handle.

5. The hand tool as in claim 4, wherein the angular orientation of the tubular tip varies depending on an angular orientation of the first lever with respect to the second lever; and
   wherein the angular orientation of the tubular tip steers an end of the wire out of the tubular tip into the hole in the bone.

6. The hand tool as in claim 3 further comprising:
   a spacing between a tubular portion of the tubular tip and the distal end of the shaft.

7. The hand tool as in claim 6, wherein the spacing exposes a portion of the wire disposed between the tubular tip and the distal end of the shaft.

8. The hand tool as in claim 3, wherein a first adjustment setting of the tubular tip on the hinge aligns a tubular section of the tubular tip and the tubular guide along a common axis; and
   wherein a second adjustment setting of the tubular tip on the hinge angularly offsets the tubular section of the tubular tip with respect to the tubular guide.

9. The hand tool as in claim 8, wherein the tubular section in the tubular tip through which the wire passes is straight; and
   wherein the tubular guide in the shaft through which the wire passes is straight.

10. The hand tool as in claim 9 further comprising:
    a spacing between the tubular section of the tubular tip and the distal end of the shaft, the spacing exposing a portion of the wire between the tubular tip and the distal end of the shaft.

11. The hand tool as in claim 10, wherein a size of the spacing between the tubular section of the tubular tip and the distal end of the shaft is smaller at the first adjustment setting than at the second adjacent setting of the tubular tip on the hinge.

12. The hand tool as in claim 1, wherein the tubular tip includes a hollow spacing between projections disposed at a location of the tubular tip that hinges the tubular tip to the distal end of the shaft, the location of the tubular tip compressed to insert the projections into receiving dimples disposed at a distal end of the shaft to provide the hinge.

13. The hand tool as in claim 1, wherein the tubular tip includes a hollow spacing between projections disposed at a location of the tubular tip that hinges the tubular tip to the distal end of the shaft, the projections extending outward from the tubular tip in an orthogonal orientation with respect to an axial length of the shaft, the location of the tubular tip compressed to insert the projections into receiving dimples disposed at a distal end of the shaft to provide the hinge.

14. The hand tool as in claim 1, wherein a tubular section in the tubular tip through which the wire passes is straight; and
   wherein a tubular guide in the shaft through which the wire passes is straight.

15. The hand tool as in claim 14, wherein the handle is a scissors handle including a first lever and a second lever;
   wherein the first lever of the scissors handle is fixedly attached to the shaft; and
   wherein the second lever of the scissors handle pivots about the first lever of the scissors handle, the second lever of the scissors handle in communication with the slidable link, the slidable link configured to slide axially along a length of the shaft and adjust the angular orientation of the tubular tip based on pivoting of the second lever with respect to the first lever of the handle; and
   wherein the angular orientation of the tubular tip varies depending on an angular orientation of the first lever with respect to the second lever.

16. The hand tool as in claim 1, wherein the wire extends through the tubular tip and out of an axial end of the tubular tip, the axial end of the tubular tip steering the wire radially outward from the axial end of the tubular tip to the medical site.

17. The hand tool as in claim 1, wherein the tubular tip includes a first opening disposed at a first axial end of the tubular tip;
   wherein the tubular tip includes a second opening at a second axial end of the tubular tip, the first axial end disposed opposite the second axial end, the first opening disposed nearer the hinge than the second opening;
   wherein the tubular tip includes a tubular section between the first opening and the second opening; and
   wherein the wire extends from the distal end of the shaft through the tubular section of the tubular tip out the second opening to the medical site.

18. A hand tool comprising:
   a shaft;
   a handle disposed at a proximal end of the shaft, the proximal end of the shaft including an opening in which to pass a wire inserted by a user operating the hand tool through the shaft; and
   a tubular tip disposed on a hinge at a distal end of the shaft, the tubular tip receiving the wire passing through the shaft, an angular orientation of the tubular tip adjustable on the hinge to steer the wire to a medical site;
   wherein the opening at the proximal end of the shaft is a first opening;
   wherein the shaft includes a second opening at the distal end of the shaft; and
   wherein the shaft is rigid and includes a tubular guide therein, the tubular guide extending through the shaft from the proximal end of the shaft to the distal end of the shaft, the tubular guide receiving and passing the wire to the tubular tip, the wire extending from the first opening through the tubular guide and through the tubular tip to the medical site, the tubular tip on the hinge extending beyond the distal end of the shaft;
   wherein a first adjustment setting of the tubular tip on the hinge aligns a tubular section of the tubular tip and the tubular guide along a common axis; and
   wherein a second adjustment setting of the tubular tip on the hinge angularly offsets the tubular section of the tubular tip with respect to the tubular guide;
   a spacing between the tubular section of the tubular tip and the distal end of the shaft, the spacing exposing a portion of the wire between the tubular tip and the distal end of the shaft;
   wherein the tubular section in the tubular tip through which the wire passes is straight; and
   wherein the tubular guide in the shaft through which the wire passes is straight;
   wherein a size of the spacing between the tubular section of the tubular tip and the distal end of the shaft is smaller at the first adjustment setting than at the second adjacent setting of the tubular tip on the hinge.

\* \* \* \* \*